United States Patent
Sudhakar et al.

(10) Patent No.: US 7,297,822 B2
(45) Date of Patent: Nov. 20, 2007

(54) 1-BROMO-4-(4'-BROMOPHENOXY)-2-PENTADECYL BENZENE AND PREPARATION THEREOF

(75) Inventors: More Arvind Sudhakar, Maharashtra (IN); Wadgaonkar Prakash Purushottam, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 27 days.

(21) Appl. No.: 11/394,144

(22) Filed: Mar. 30, 2006

(65) Prior Publication Data

US 2006/0264680 A1    Nov. 23, 2006

(30) Foreign Application Priority Data

Mar. 31, 2005    (IN)    ............... 798/DEL/2005

(51) Int. Cl.
     *C07C 43/205*    (2006.01)
     *C07C 41/09*    (2006.01)

(52) U.S. Cl. .................................................. 568/639
(58) Field of Classification Search ................. 568/639
See application file for complete search history.

(56) References Cited

U.S. PATENT DOCUMENTS

| | | | | |
|---|---|---|---|---|
| 4,252,624 A | * | 2/1981 | Stephan ................. | 204/157.92 |
| 4,835,322 A | * | 5/1989 | Mamuzic et al. ........... | 568/639 |
| 5,741,949 A | * | 4/1998 | Mack ......................... | 568/639 |

* cited by examiner

*Primary Examiner*—Rosalynd Keys
(74) *Attorney, Agent, or Firm*—Meyertons, Hood, Kivlin, Kowert & Goetzel, P.C.

(57) ABSTRACT

The present invention relates to novel brominated phenoxy compounds and to process for their preparation. More particularly, the present invention relates to synthesis of novel dibromodiphenyl ether starting from Cashew Nut Shell Liquid (CNSL);—a renewable resource material. The present invention particularly relates to novel 1-bromo-4-(4'-bromophenoxy)-2-pentadecylbenzene and to a method for it's preparation.

8 Claims, No Drawings

1-BROMO-4-(4'-BROMOPHENOXY)-2-PENTADECYL BENZENE AND PREPARATION THEREOF

FIELD OF INVENTION

This invention relates to a novel 1-bromo-4-(4'-bromophenoxy)-2-pentadecyl benzene and a process for the preparation preparation thereof. More particularly, the present invention relates to a novel brominated phenoxy compound of formula (1)

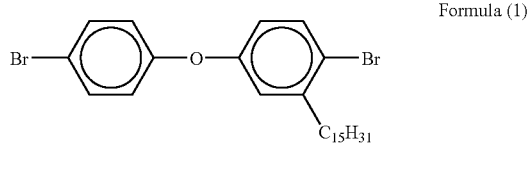

Formula (1)

and a process for the preparation thereof. Still more particularly, the present invention relates to the synthesis of compound of formula (1) starting from Cashew Nut Shell Liquid (CNSL);—a renewable resource material.

BACKGROUND OF INVENTION

Cashew nut shell liquid (CNSL) is a renewable resource material, which is cheap and commercially available and is useful in various areas of chemical industry, such as plastics production. Technical grade CNSL comprises a major proportion (typically about 80% by wt) of a material sold commercially under the trade name CARDANOL which comprises a mixture of 3-(pentadec-8-enyl) phenol, 3-(pentadec-8, 11-dienyl) phenol, and 3-(pentadec-8,11,14-trienyl) phenol. Minor constituents include about 18% by wt. of a material also sold separately under the trade name CARDOL, which is a mixture of the corresponding 5-substituted resorcinols and about 2% by wt. of 2-methyl cardol, which is a mixture of corresponding 2-methyl-5-substituted resorcinols, and other materials.

The level of interest in developing new dibrominated phenoxy compounds is derived from the fact that these brominated compounds can be used as precursors of difunctional monomers or themselves as difunctional monomers and hence polymers. These compounds are useful as starting materials for the synthesis of a variety of 4,4'-disubstituted diphenyl ethers such as diiodides, diamines, dicarboxylic acids, diphenols, diboronic acids/diboronic esters etc. by employing known organic transformations. These 4,4'-disubstituted diphenyl ethers are useful condensation (difunctional) monomers for the production of high performance polymers employing metal-catalyzed polymerizations such as Suzuki polycondensation, Ni-catalysed polycondensation or Zn-catalysed polycondensation. They can also be polymerized using CO and various nucleophiles (e.g., diamines, diacylhydrazides, diphenols, aminophenols, etc) in the presence of palladium catalysts to yield the corresponding high-molecular-mass products.

It is well known in the prior art that incorporation of a long alkyl chain in polymer backbone imparts processability to the polymer. The improved properties they provide can benefit a wide range of applications, which seek better performance with improved processability. It is therefore of great interest and importance to synthesize new brominated phenoxy compounds with alkyl radical in their structure, more particularly from CNSL which is readily available commercially and is a renewable resource material.

There is no prior art available for the preparation of 1-bromo-4-(4'-bromophenoxy)-2-pentadecyl benzene and the inventors of the present invention are reporting the said compound and it's preparation using CNSL for the first time.

OBJECTINESS OF THE INVENTION

The main object of the present invention is to provide 1-bromo-4-(4'-bromophenoxy)-2-pentadecyl benzene of formula (1)

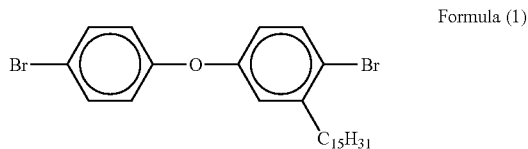

Formula (1)

Another object of the invention is to provide a class of novel bromophenoxy compounds starting from naturally occurring renewable CNSL thereby providing a process for the preparation of the said compound.

SUMMARY OF THE INVENTION

The present invention provides novel brominated phenoxy compound starting from naturally occurring and renewable resource material such as CNSL, which is useful in the preparation of a variety of 4,4'-disubstituted diphenyl ethers, which can be utilized as precursors of difunctional monomers or itself as a monomer for the synthesis of polymers.

Accordingly the present invention provides a novel 1-bromo-4-(4'-bromophenoxy)-2-pentadecyl benzene having the formula 1

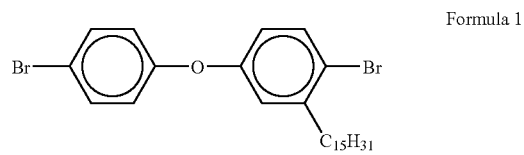

Formula 1

The present invention further provides a process for the preparation of 1-bromo-4-(4'-bromophenoxy)-2-pentadecyl benzene of formula 1, which comprises reacting 3-pentadecyl phenol with a metal hydroxide in the presence of a mixture of solvents consisting of high boiling polar solvent and an aromatic hydrocarbon solvent, at a temperature in the range of 120-150° C. for at least 7 hours, removing the aromatic hydrocarbon solvent by known method, treating the above said reaction mixture with halobenzene in the presence of Cu powder, at a temperature in the range of 120-150° C. for at least 8 hours, removing the high boiling polar solvent and Cu salt by known method, extracting the filtrate in an organic solvent, washing the above said solvent extract with water to obtain a solution containing 1-pentadecyl-3-phenoxy benzene, removing the solvent and purifying the resultant crude 1-pentadecyl-3-phenoxy benzene by known method, brominating the above said 1-pentadecyl-3-phenoxy benzene in dark by brominating agent in a halogenated hydrocarbon solvent, at a temperature below 5° C., heating the above said reaction mixture at a temperature in the range of 30-40° C., continuing the reaction for at least 12 hrs, removing the excess bromine by known method and extracting the reaction mixture in halogenated hydrocarbon followed by washing with water, removing the solvent and further purifying the resultant product by known method to obtain the desired 1-bromo-4-(4'-bromophenoxy)-2-pentadecyl benzene in pure form.

In an embodiment of the present invention the metal hydroxide used is an alkali metal hydroxide selected from potassium hydroxide and sodium hydroxide.

In yet another embodiment the aromatic hydrocarbon solvent used is toluene.

In yet another embodiment the high boiling polar solvent used is selected from N,N-dimethylacetamide, N,N-dimethylformamide.

In yet another embodiment the brominating agent used is selected from $Br_2$, dibromodimethylhydantoin and bromine generated insitu by employing HBr together with an oxidizing agent selected from $H_2O_2$, t-BuOOH and $NaBrO_3$.

In yet another embodiment the temperature used for bromination reaction is in the range of −5 to 0° C.

In yet another embodiment the halogenated hydrocarbon used is dichloromethane.

In yet another embodiment the 3-pentadecyl phenol is obtained from commercially available CNSL by conventional methods known in the art.

DETAILED DESCRIPTION OF THE INVENTION

The present invention relates to the novel 1-bromo-(4-bromophenoxy)-2-pentadecyl benzene, useful for the preparation of a variety of 4,4'-disubstituted diphenyl ether monomers and polymers thereof. The compound of the invention is of formula (1)

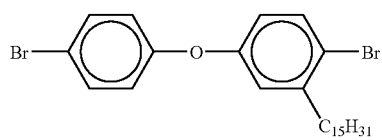

Formula (1)

The compound of formula (1), viz. 1-bromo-4-(4'-bromophenoxy)-2-pentadecyl benzene is prepared by first reacting 3-pentadecyl phenol formula (2)

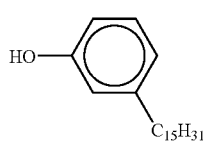

Formula (2)

with halobenzene.

The first step of the process of the invention comprises reaction of 3-pentadecyl phenol with halobenzene in presence of metal hydroxide and Cu as a catalyst to obtain the corresponding 1-pentadecyl-3-phenoxy benzene; under classical Ullmann etherification reaction. Typical Ullmann etherification reaction uses Cu-powder/Cu salts as catalyst (Ullmann, F. *Chem. Ber.,* 1904, 37, 853; Lindley, J. *Tetrahedron,* 1984, 40, 1433). There are several other reagents available for Ullmann etherification reaction such as by using Pd $(DBA)_2$/dppf (*Tett. Lett.,* 1977, 38, 8005), $Pd(OAc)_2$/aryldialkyl phosphines as a ligand (*J. Am. Chem. Soc.,* 1999, 121, 4369), $(CuOTf)_2.PhH/EtOAc/Cs_2CO_3$/ArCOOH (*J. Am. Chem. Soc.,* 1997, 119, 10539). CuI/N,N-dimethyl glycine. HCl salt/$Cs_2CO_3$ (*Org. Lett.,* 2003, 5, 3799), $CuCl/Cs_2CO_3$/2,2,6,6-tetramethylheptane-3,5-dione (*Org. Lett.,* 2002, 4, 1623), phosphazene $P_4$-t-Bu base/CuBr (*Chem. Commun.,* 1998, 2091), $CuI/K_2CO_3$/Raney Ni—Al alloy (*Synlett,* 2003, 13, 2071), $CuCO_3.Cu(OH)_2.H_2O$/ $K_3PO_4$ and $[Cu(CH_3CN)_4]ClO_4$ etc.

In the first step of the of the process of preparation of 1-pentadecyl-3-phenoxy benzene in the invention, the metal hydroxides employed can be any metal hydroxide capable of forming metal salt with hydroxyl radical of the substituted phenol. Illustrative metal hydroxides are potassium hydroxide, sodium hydroxide or the like. The employed catalyst in the etherification reaction of the invention is preferably Cu salts.

In the present invention, the process for the preparation of 1-pentadecyl-3-phenoxy benzene comprises potassium hydroxide as a base and Cu powder as a catalyst. The temperatures are typically in the range of 120-150° C. The amount of potassium hydroxide is slight excess over stoichiometric amount, typically about 0.2-0.5 mol excess. The amount of Cu powder as a catalyst is most often 2 wt %. The solvent system employed in the process in present invention is a mixture of N,N-dimethylacetamide and toluene is preferred.

The final step comprises of brominating the obtained 1-pentadecyl-3-phenoxy benzene. Any suitable brominating agent can be used in the bromination reaction, as long as it is compatible with the reaction mixture. Preferred brominating agents include, e.g., $Br_2$, or bromine may be generated insitu e.g., by employing HBr together with an oxidizing agent such as $H_2O_2$ or $NaBrO_3$ or the like known oxidizing agents. Various methods of bromination of diphenyl ether have been described in number of patents such as U.S. Pat. Nos. 4,835,322, 4,214,103, 3,285,965, 2,022,634 and British patent No. 1,472,383. The reaction can be carried out in a solvent or without solvent but the presence or absence of a solvent may affect the selectivity of the bromination. When a solvent is employed, it is preferred to employ such a solvent, which is unreactive under the reaction conditions such as halocarbons e.g., dichloromethane, carbon tetrachloride, and 1,2-dichloroethane. The reaction temperature also affects the selectivity and reaction rate. It is preferred to add brominating agent at a temperature in the range of about −10° C. to 25° C., and to carry out the reaction at a temperature in the range of about −10° C. to 90° C.

The intermediates and products in each step of the reaction can be worked up and isolated by any conventional means, such as solvent removal when a solvent is employed, washing, drying, recrystallisation and column chromatography.

The invention will now be described by the following examples, which are illustrative and should not be construed as limiting the scope of invention in any manner.

EXAMPLE—1

Into a two necked round bottom flask fitted with a Dean and Stark assembly with a reflux condenser were taken 100 g (0.33 mol) of 3-pentadecyl phenol; 22.06 g (0.39 mol) potassium hydroxide along with 300 ml N,N-dimethylacetamide and 150 ml toluene. The reaction mixture was refluxed for 7 hours and the byproduct; water formed was removed from the reaction mixture. After completion of the reaction, the solvent was distilled off and the dark sticky product was dried at vacuum. The compound obtained was potassium salt of 3-pentadecyl phenol in a yield of 112 g (99% of the theoretical).

To a round bottom flask containing 111 g potassium salt of 3-pentadecylphenol (0.32 mol) was added 50.88 g (0.32 mol) of bromobenzene, followed by 2.22 g Cu powder (2 wt %) along with 150 ml N,N-dimethylacetamide. The reaction mixture was then heated at 150° C. for 8 hours. After completion of the reaction the obtained dark colored solution was poured into 500 ml water; the Cu salts were removed by filtration; The filtrate was extracted with ethyl acetate, thoroughly washed with water followed by saturated aqueous sodium chloride solution and dried over sodium sulfate. Solvent evaporation yielded crude 1-pentadecyl-3-phenoxy benzene. Pure 1-pentadecyl-3-phenoxy benzene was obtained after silica gel (60-120 mesh) column chromatography (pet ether) 70 g (57% of the theoretical).

EXAMPLE—2

Into a three necked round bottom flask equipped with a stirrer, a condenser, a dropping funnel and a thermometer; containing a stirred solution of 25 g (0.066 mol) 1-pentadecyl-3-phenoxy benzene in 150 ml dichloromethane, was added dropwise 22.08 g (0.14 mol) of $Br_2$ protecting from light. The top of the condenser was equipped with a trap to absorb the HBr released during the reaction. $Br_2$ was added at a temperature between −5° to 0° C. and during 15 minutes. After the addition the reaction mixture was stirred at the same temperature for 1 hour and then refluxed overnight.

After completion of reaction excess bromine and HBr were neutralized with aqueous 10% $NH_3$ (100 ml). Two phases formed in the reaction, were separated, and the organic layer was washed with water (300 ml), after drying of a solvent and distillation crude 1-bromo-4-(4'-bromophenoxy)-2-pentadecyl benzene was obtained. After silica gel (60-120 mesh) column purification 1-bromo-(4-bromophenoxy)-2-pentadecyl benzene was obtained in pure form Yield 30 g (84% of the theoretical).

ADVANTAGES OF THE INVENTION

The present invention provides a simple procedure for the synthesis of novel brominated phenoxy compounds; which has the potential to act as precursor of monomers, themselves as monomers which are useful for the synthesis high performance polymers with excellent processability by virtue of presence of pentadecyl chain.

The process of the invention is economical since it uses CNSL as the starting material, a naturally occurring and renewable resource material.

We claim:

1. A novel 1-bromo-4-(4'-bromophenoxy)-2-pentadecyl benzene having the formula

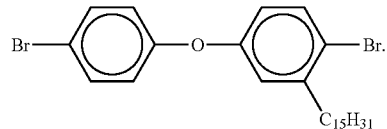

2. A process for the preparation of 1-bromo-4-(4'-bromophenoxy)-2-pentadecyl benzene of formula 1, which comprises reacting 3-pentadecyl phenol with a metal hydroxide in the presence of a mixture of solvents consisting of high boiling polar solvent and an aromatic hydrocarbon solvent, at a temperature in the range of 120-150° C. for at least 7 hours, removing the aromatic hydrocarbon solvent by known method, treating the above said reaction mixture with halobenzene in the presence of Cu powder, at a temperature in the range of 120-150° C. for at least 8 hours, removing the high boiling polar solvent and Cu salt by known method, extracting the filtrate in an organic solvent, washing the above said solvent extract with water to obtain a solution containing 1-pentadecyl-3-phenoxy benzene, removing the solvent and purifying the resultant crude 1-pentadecyl-3-phenoxy benzene by known method, brominating the above said 1-pentadecyl-3-phenoxy benzene in dark by brominating agent in a halogenated hydrocarbon solvent, at a temperature below 5° C., heating the above said reaction mixture at a temperature in the range of 30-40° C., continuing the reaction for at least 12 hrs, removing the excess bromine by known method and extracting the reaction mixture in halogenated hydrocarbon followed by washing with water, removing the solvent and further purifying the resultant product by known method to obtain the desired 1-bromo-4-(4'-bromophenoxy)-2-pentadecyl benzene in pure form.

3. A process according to claim 2, wherein the metal hydroxide used is an alkali metal hydroxide selected from the group consisting of potassium hydroxide and sodium hydroxide.

4. A process according to claim 2, wherein the aromatic hydrocarbon solvent used is toluene.

5. A process according to claim 2, wherein the high boiling polar solvent used is selected from the group consisting of N,N-dimethylacetamide and N,N-dimethylformamide.

6. A process according to claim 2, wherein the brominating agent used is selected from $Br_2$, dibromodimethylhydantoin and bromine generated insitu by employing HBr together with an oxidizing agent selected from the group consisting of $H_2O_2$, t-BuOOH and $NaBrO_3$.

7. A process according to claim 2, wherein the temperature used for bromination reaction is in the range of −5 to 0° C.

8. A process according to claim 2, wherein the halogenated hydrocarbon used is dichloromethane.

* * * * *